United States Patent
Wigglesworth et al.

(10) Patent No.: US 8,742,403 B2
(45) Date of Patent: Jun. 3, 2014

(54) XANTHENE BASED SEMICONDUCTOR COMPOSITIONS

(75) Inventors: Anthony J. Wigglesworth, Oakville (CA); Yiliang Wu, Oakville (CA); Ping Liu, Mississauga (CA); Nan-Xing Hu, Oakville (CA)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 497 days.

(21) Appl. No.: 13/043,206

(22) Filed: Mar. 8, 2011

(65) Prior Publication Data

US 2012/0228584 A1    Sep. 13, 2012

(51) Int. Cl.
H01L 51/30    (2006.01)
H01B 1/12    (2006.01)
C07D 311/78    (2006.01)

(52) U.S. Cl.
USPC ...... 257/40; 257/E51.027; 252/500; 252/502; 549/381

(58) Field of Classification Search
None
See application file for complete search history.

(56) References Cited

U.S. PATENT DOCUMENTS

| | | |
|---|---|---|
| 7,256,418 B2 | 8/2007 | Ong et al. |
| 2005/0082525 A1 | 4/2005 | Heeney et al. |
| 2005/0277776 A1 | 12/2005 | Liu et al. |
| 2007/0112171 A1 | 5/2007 | Li et al. |
| 2007/0145357 A1 | 6/2007 | Wu et al. |
| 2007/0145371 A1 | 6/2007 | Wu et al. |
| 2007/0145453 A1 | 6/2007 | Wu et al. |
| 2007/0148812 A1 | 6/2007 | Wu et al. |
| 2007/0235719 A1 | 10/2007 | Ong et al. |
| 2007/0235726 A1 | 10/2007 | Li et al. |
| 2007/0284572 A1 | 12/2007 | Ong et al. |
| 2008/0006324 A1 | 1/2008 | Berke et al. |
| 2008/0009625 A1* | 1/2008 | Brown et al. ............ 546/49 |
| 2008/0102559 A1 | 5/2008 | Ong et al. |
| 2008/0103286 A1 | 5/2008 | Ong et al. |
| 2008/0103314 A1 | 5/2008 | Li et al. |
| 2008/0108833 A1 | 5/2008 | Ong et al. |
| 2008/0108834 A1 | 5/2008 | Ong et al. |
| 2008/0146776 A1 | 6/2008 | Liu et al. |
| 2009/0114909 A1 | 5/2009 | Li et al. |
| 2009/0124788 A1 | 5/2009 | Li et al. |
| 2009/0140236 A1 | 6/2009 | Wu et al. |
| 2009/0140237 A1 | 6/2009 | Wu et al. |
| 2009/0179194 A1 | 7/2009 | Wu et al. |
| 2009/0179198 A1 | 7/2009 | Bailey et al. |
| 2009/0181509 A1 | 7/2009 | Pan et al. |
| 2009/0217980 A1 | 9/2009 | Pfeiffer et al. |
| 2009/0256138 A1 | 10/2009 | Wu et al. |
| 2009/0256139 A1 | 10/2009 | Wu et al. |
| 2010/0078074 A1 | 4/2010 | Yang et al. |
| 2011/0040069 A1 | 2/2011 | Miura et al. |

FOREIGN PATENT DOCUMENTS

| | | |
|---|---|---|
| JP | 2007-246579 A | 9/2007 |
| JP | 2010-109360 A | 5/2010 |
| WO | WO 2005/014688 A2 | 2/2005 |
| WO | WO 2010/036494 A1 | 4/2010 |
| WO | WO 2010/135701 A1 | 11/2010 |
| WO | 2307483 A | 4/2011 |

OTHER PUBLICATIONS

J. Hou et al., *Bandgap and Molecular Energy Level Control of Conjugated Polymer Photovoltaic Materials Based on Benzo[1,2-b:4,5-b']dithiophen*, Macromolecules, 2008, 41, 6012-6018.
H. Usta et al. *Air-Stable, Solution-Processable n-Channel and Ambipolar Semiconductors for Thin-Film Transistors Based on the Indenofluorenehis(dicyanovinylene) Core*, J. Am. Chem. Soc. 2008, 130 (27), 8580-8581.
J. Sakamoto et al., *Suzuki Polycondensation: Polyarylenes à la Carte*, Macromol. Rapid Commun. 2009, 30, 653-687.
M. Zhang et al., *Field-Effect Transistors Based on a Benzothiadiazole—Cyclopentadithiophene Copolymer*, J. Am. Chem. Soc., 2007, 129, 3472-3473.

(Continued)

Primary Examiner — Andrew K Bohaty
(74) Attorney, Agent, or Firm — Harness, Dickey & Pierce, P.L.C.

(57) ABSTRACT

A small molecule semiconductor of Formula (I):

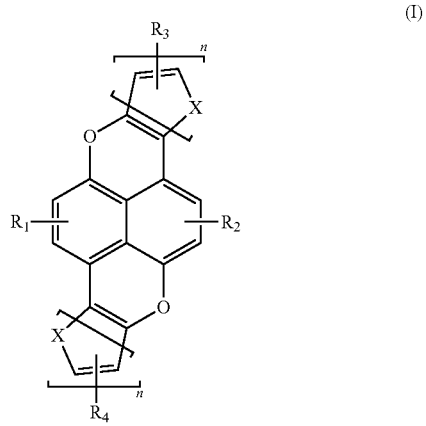

wherein $R_1$, $R_2$, $R_3$ and $R_4$ are independently selected from a hydrogen atom, a substituted or unsubstituted alkyl group, a substituted or unsubstituted alkenyl group, a substituted or unsubstituted ethynyl group, a substituted or unsubstituted aryl group, a substituted or unsubstituted heteroaryl group, an alkoxy group, an alkylthio group, an alkylsilyl group, a cyano group, and a halogen atom, wherein n is 1 or 2, and wherein X is independently S or

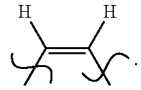

17 Claims, 2 Drawing Sheets

(56) References Cited

OTHER PUBLICATIONS

Y. Liang et al., *Development of New Semiconducting Polymers for High Performance Solar Cells*, J. Am. Chem. Soc. 2009, 131, 56-57.

Chao-Ying Yu et al., *Thiophene/Phenylene/Thiophene-Based Low-Bandgap Conjugated Polymers for Efficient Near-Infrared Photovoltaic Applications*, Chem. Materials, vol. 21, No. 14, 2009, pp. 3262-3269.

U.S. Appl. No. 12/575,701, filed Oct. 8, 2009.

T. Terao et al., *Palladium-Catalyzed Cross-Coupling of Benzyl Ketones and α,β-Unsaturated Carbonyl and Phenolic Compounds with o-Dibromobenzenes to Produce Cyclic Products*, Bull. Chem. Soc. Jpn., vol. 72, 1999, pp. 2345-2350.

C. Du et al., *Fused-seven ring Anthracene Derivative With two Sulfur Bridges for High Performance Red Organic light-emitting Diodes*, The Royal Society of Chemistry, 2010, 3 pgs.

U.S. Appl. No. 12/689,613, filed Jan. 19, 2010.

Office Action for U.S. Appl. No. 12/689,613, mailed Feb. 25, 2010.

Pan, et al., "Low-Temperature, Solution-Processed, High-Mobility Polymer Semiconductors for Thin-Film Transistors," J. Am. Chem. Soc., 2007, vol. 129, pp. 4112-4113.

Great Britain Search Report in Great Britain Application No. GB 1100733.3, dated May 17, 2011.

Office Action mailed May 24, 2012 issued in U.S. Appl. No. 12/689,613.

Foreign search report dated Mar. 20, 2012 issued in German Patent Application No. 10 2011 002 579.0, and English translation.

Office Action dated Jul. 5, 2012 issued in Canadian Patent Application No. 2,727,497.

Office Action in U.S. Appl. No. 12/689,613 mailed Jul. 15, 2011.

Office Action mailed Dec. 8, 2011 issued in U.S. Appl. No. 12/689,613.

\* cited by examiner

XANTHENE BASED SEMICONDUCTOR COMPOSITIONS

BACKGROUND

Fabrication of printed organic electronics (POE) is of profound interest, as such devices are ultra-low cost, are solution processable, and possess mechanical durability and structural flexibility. One type of POE, a printed thin-film transistor (TFT), has received much attention in recent years as it is a promising, low cost alternative to silicon technology for application in, for example, active-matrix liquid crystal displays (LCDs), organic light emitting diodes, e-paper, radio frequency identification tags (RFIDs), photovoltaics, and the like.

TFTs are generally composed of a supporting substrate, three electrically conductive electrodes (gate, source and drain electrodes), a channel semiconductor layer, and an electrically insulating gate dielectric layer separating the gate electrode from the semiconductor layer. It is desirable to improve the performance of known TFTs. Performance can be measured by at least two properties: mobility, and the on/off ratio. Mobility is measured in units of $cm^2/V \cdot sec$; higher mobility is desired. The on/off ratio is the ratio between the amount of current that leaks through the TFT in the off state versus the current that runs through the TFT in the on state. Typically, a higher on/off ratio is more desirable.

Organic thin-film transistors (OTFTs) can be used in applications such as radio frequency identification (RFID) tags and backplane switching circuits for displays, such as signage, readers, and liquid crystal displays, where high switching speeds and/or high density are not essential. They also have attractive mechanical properties such as being physically compact, lightweight, and flexible.

The semiconducting layers of OTFTs can be fabricated using low-cost solution-based patterning and deposition techniques, such as spin coating, solution casting, dip coating, stencil/screen printing, flexography, gravure, offset printing, ink jet-printing, micro-contact printing, and the like. To enable the use of these solution-based processes in fabricating thin-film transistor circuits, solution processable materials are therefore required. However, organic or polymeric semiconductors formed by solution processing tend to suffer from limited solubility, air sensitivity, and especially low field-effect mobility. This poor performance may be attributable to the poor film-forming nature of small molecules.

Despite the advances in the development of semiconducting polymers and related materials for use in photovoltaic devices, a need exists for materials and materials processing that (1) improve the performance of these devices, (2) maintain a good solubility in non-toxic solvents and (3) have a good environmental stability. The present application seeks to fulfill this need and provides further related advantages.

SUMMARY

The present application thus achieves advances over prior semiconductors and discloses a small molecule semiconductor of Formula (I):

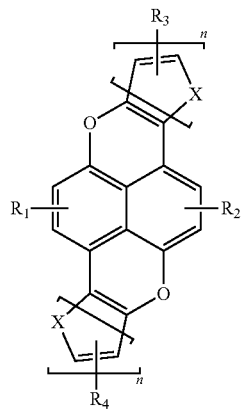

wherein $R_1$, $R_2$, $R_3$ and $R_4$ are independently selected from a hydrogen atom, a substituted or unsubstituted alkyl group, a substituted or unsubstituted alkenyl group, a substituted or unsubstituted ethynyl group, a substituted or unsubstituted aryl group, a substituted or unsubstituted heteroaryl group, an alkoxy group, an alkylthio group, an alkylsilyl group, a cyano group, and a halogen atom, wherein n is 1 or 2, and wherein X is independently S or

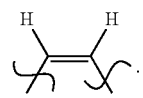

In embodiments, described herein is a semiconductor composition comprising: a polymer binder; and a small molecule semiconductor of Formula (I):

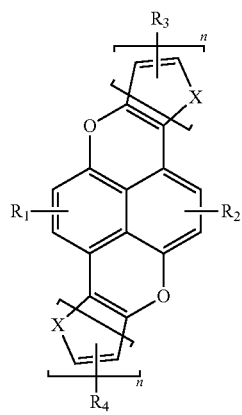

wherein $R_1$, $R_2$, $R_3$ and $R_4$ are independently selected from a hydrogen atom, a substituted or unsubstituted alkyl group, a substituted or unsubstituted alkenyl group, a substituted or unsubstituted ethynyl group, a substituted or unsubstituted aryl group, a substituted or unsubstituted heteroaryl group, an alkoxy group, an alkylthio group, an alkylsilyl group, a cyano group, and a halogen atom, wherein n is 1 or 2, and wherein X is independently S or

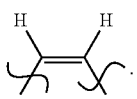

In embodiments, described herein is an electronic device comprising a semiconducting layer, the semiconducting layer comprising: a small molecule semiconductor of Formula (I):

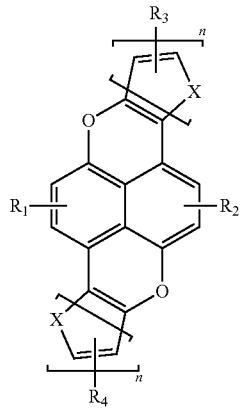

(I)

wherein $R_1$, $R_2$, $R_3$ and $R_4$ are independently selected from a hydrogen atom, a substituted or unsubstituted alkyl group, a substituted or unsubstituted alkenyl group, a substituted or unsubstituted ethynyl group, a substituted or unsubstituted aryl group, a substituted or unsubstituted heteroaryl group, an alkoxy group, an alkylthio group, an alkylsilyl group, a cyano group, and a halogen atom, wherein n is 1 or 2, and wherein X is independently S or

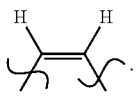

EMBODIMENTS

Figure 1:
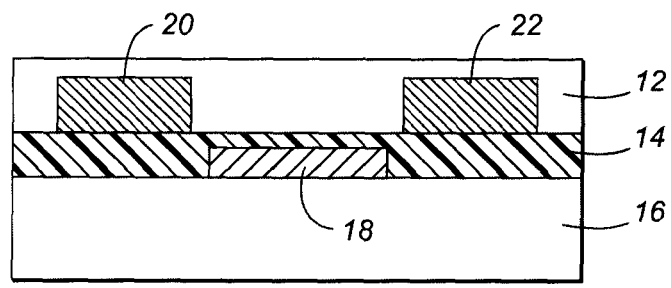
FIGS. 1 and 2 illustrate various representative embodiments of the present disclosure, wherein small molecule semiconductors of the formulas as illustrated herein are selected as the semiconductor material in thin-film transistor (TFT) configurations.

The present disclosure relates to small molecule semiconductor compounds having a fused xanthene core as disclosed herein. Compositions comprising a polymer binder and the small molecule semiconductor are also disclosed. A semiconducting layer formed from the composition is very stable in air and has high mobility. These semiconductor compositions are useful for forming layers, such as semiconducting layers, in electronic devices, such as thin film transistors (TFTs).

Xanthene based semiconducting compounds are important materials for organic thin-film transistors and organic polymer solar cells. "Xanthene based" is defined herein as materials possessing at least one oxaanthracene subunit or at least one thienochromoene subunit in the semiconductor core. The chemical formulas of oxaanthracene and thienochromene are shown below.

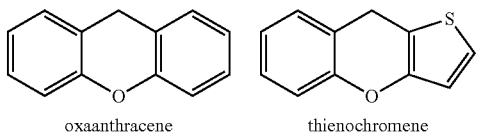

oxaanthracene   thienochromene

This material is soluble (allowing for ease of use in manufacturing) and exhibits high field-effect mobility in TFTs without requiring a thermal annealing step during device fabrication.

The xanthene core itself has low solubility in organic solvents. However, with some modification, soluble xanthene based semiconducting compounds may include a small molecule semiconductor having the structure of Formula (I):

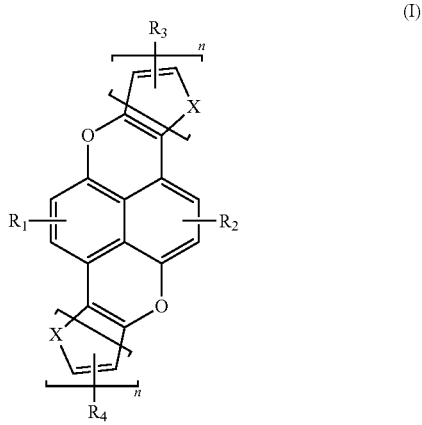

(I)

wherein $R_1$, $R_2$, $R_3$ and $R_4$ are independently selected from a hydrogen atom, a substituted or unsubstituted alkyl group, a substituted or unsubstituted alkenyl group, a substituted or unsubstituted ethynyl group, a substituted or unsubstituted aryl group, a substituted or unsubstituted heteroaryl group, an alkoxy group, an alkylthio group, an alkylsilyl group, and a heteroatom, such as a halogen atom, wherein n is 1 or 2, and wherein X is independently S or

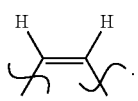

The phrase "small molecule" is defined herein as a compound having a molecular weight less than about 1500 Daltons, such as less than about 1000 Daltons.

The term "substituted" refers to at least one hydrogen atom on the named radical being substituted with another functional group, such as halogen, —CN, —NO$_2$, —COOH, and —SO$_3$H. An exemplary substituted alkyl group is a perhaloalkyl group, wherein one or more hydrogen atoms in an alkyl group are replaced with halogen atoms, such as fluorine, chlorine, iodine, and bromine. Besides the aforementioned functional groups, an aryl group may also be substituted with alkyl, alkoxy, or alkylthio. Exemplary substituted aryl groups include propylphenyl and propoxyphenyl.

The term "alkyl" refers to a radical composed entirely of carbon atoms and hydrogen atoms that is fully saturated and of the formula —$C_nH_{2n+1}$. The alkyl radical may be linear, branched, or cyclic, and contain from about 3 to about 50 carbon atoms, from about 4 to about 40 carbon atoms, from about 5 to about 36 carbon atoms and from about 8 to about 24 carbon atoms.

The term "alkenyl" refers to a radical that contains at least one carbon-carbon double bond that is not part of an aryl or heteroaryl structure. The alkenyl radical may be linear, branched, or cyclic, and may include heteroatoms. Exemplary alkenyl radicals include arylalkenyl radicals like 2-phenylethenyl or 2-naphthylethenyl; and heteroarylalkenyl radicals like 2-thienylethenyl.

The term "ethynyl" refers to a radical composed entirely of carbon atoms and hydrogen atoms that contains at least one carbon-carbon triple bond.

The term "aryl" refers to an aromatic radical composed entirely of carbon atoms and hydrogen atoms. When aryl is described in connection with a numerical range of carbon atoms, it should not be construed as including substituted aromatic radicals. For example, the phrase "aryl containing from 6 to 10 carbon atoms" should be construed as referring to a phenyl group (6 carbon atoms) or a naphthyl group (10 carbon atoms) only, and should not be construed as including a methylphenyl group (7 carbon atoms). However, the aryl group may be substituted with additional substituents such as an alkyl group, an alkoxy group, an alkylthio group, a cyano group and a halogen.

The term "heteroaryl" refers to an aromatic radical composed of carbon atoms, hydrogen atoms, and one or more heteroatoms. The carbon atoms and the heteroatoms are present in a cyclic ring or backbone of the radical. The heteroatoms are selected from O, S, and N. Exemplary heteroaryl radicals include thienyl and pyridinyl.

The term "alkoxy" refers to an alkyl radical, which is attached to an oxygen atom, such as —O—$C_nH_{2n+1}$, wherein n is from 1 to 30, from 3 to 24, from 3 to 16 and from 6 to 16.

The term "alkylthio" refers to an alkyl radical that is attached to a sulfur atom, i.e. —S—$C_nH_{2n+1}$, wherein n is from 1 to 30, from 3 to 24, from 3 to 16 and from 6 to 16.

The term "alkylsilyl" refers to a radical composed of a tetravalent silicon atom having three alkyl radicals attached to the silicon atom, i.e. —$Si(R)_3$, wherein R is an alkyl as defined. The three alkyl radicals may be the same or different.

Generally, the alkyl and alkoxy groups each independently contain from 1 to 30 carbon atoms. Similarly, the aryl and heteroaryl groups independently contain from 4 to 30 carbon atoms.

As noted above, X in the same molecule may be the same or different. In particular embodiments, X of Formula (I) may be a sulfur atom (S) or

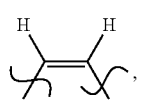

and n may be 1 or 2. By defining X in the manner described above, the small molecule semiconductor have a xanthene core may be fused with a thiophene, benzene or a naphthalene. Specific examples include those shown in Formulas (I-a) through (I-d):

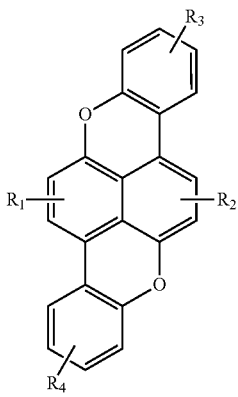

(I-a)

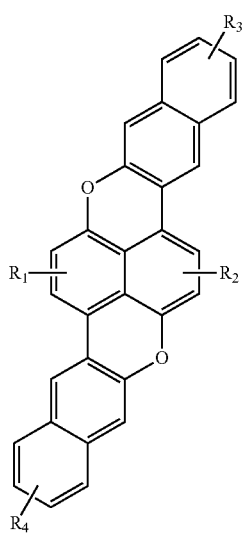

(I-b)

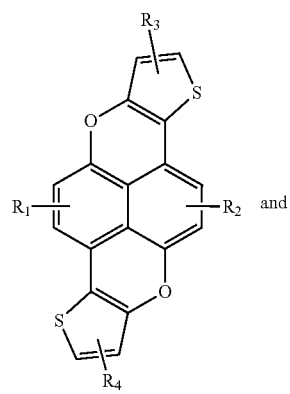

(I-c)

and

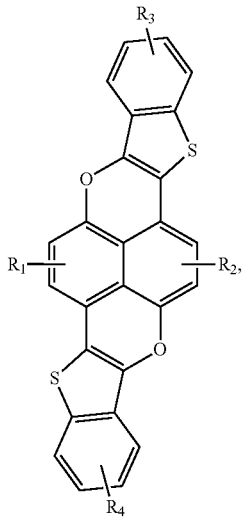

(I-d)

wherein $R_1$, $R_2$, $R_3$ and $R_4$ are independently selected from a hydrogen atom, a substituted or unsubstituted alkyl group, a substituted or unsubstituted alkenyl group, a substituted or unsubstituted ethynyl group, a substituted or unsubstituted aryl group, a substituted or unsubstituted heteroaryl group, an alkoxy group, an alkylthio group, an alkylsilyl group, and a halogen atom.

The small molecule semiconductor compounds having a fused xanthene core may also be represented by compounds having the structure of formula (II),

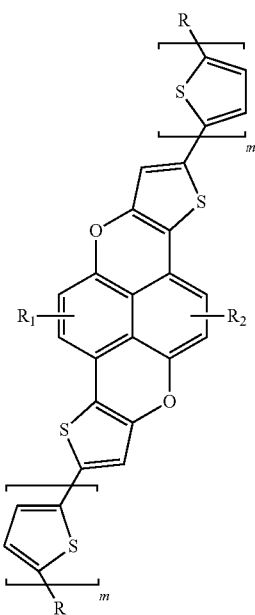

(II)

wherein R is independently selected from a hydrogen atom, a substituted or unsubstituted alkyl group, a substituted or unsubstituted alkenyl group, a substituted or unsubstituted ethynyl group, a substituted or unsubstituted aryl group, an alkoxy group, an alkylthio group, an alkylsilyl group, and a halogen atom, and wherein m is from 1 to 10, from 1 to 5 and 1 to 3.

In embodiments, the small molecule semiconductor has a band gap of from about 1.6 to about 3.0 eV. This large band gap typically means that the small molecule semiconductor has better stability in air, when compared to a pentacene-based semiconductor. The small molecule semiconductor has a crystalline or liquid crystalline structure.

This xanthene semiconductor core can be synthesized, for example, by coupling a dihydroxynaphthalene compound with a dihalogenated arene compound using a palladium catalyzed cross-coupling reaction. Examples of dihydroxynapthalene compounds, such as 1,5-dihydroxynaphthalene, 2,6-dichloro-1,5-dihydroxynaphthalene, and 2,6-dihexyl-1,5-dihydroxynaphthalene.

Examples of the halogenated arene compound include those compounds represented by Formula (III):

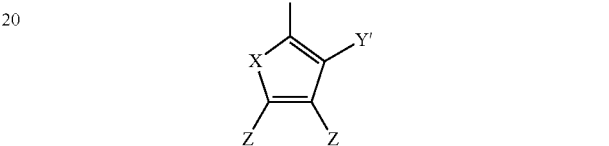

(III)

wherein X is a sulfur (S) or a

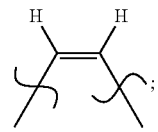

Y and Y' are a hydrogen atom or fused aromatic ring, such as, for example, a fused benzene ring or a fused thiophene ring, and Z is independently a halogen atom, such as, for example, chlorine, bromine, iodine, fluorine. Specific examples of the halogenated arene compound may include, but are not limited to, 1,2-dibromobenzene, 1,2-dibromo-5,6-dimethylbenzene, 3,4-dibromotoluene, 2,3-dibromonaphthalene, 2,3-dibromo-6,7-dicyanonaphthalene, 2,3-dibromothiophene, 2,3-dibromo-5-hexylthiophene and 2,3-dibromo[1]benzothiophene.

The xanthene semiconductor core may be synthesized using palladium cross-coupling techniques. Examples of these techniques include a palladium catalyzed Heck oxyarylation reaction, wherein a mixture comprised of a substituted or unsubstituted 1,5-dihydroxynapthalene compound and a dihalogenated aromatic compound is treated with a base in the presence of a palladium catalyst and a solvent. Example bases include alkali metal bases such as, for example, $K_2CO_3$, $Cs_2CO_3$, KOt-Bu, KF, CsF and $K_3PO_4$. Examples of the palladium catalyst may include $PdOAc_2$:$PPh_3$, $PdOAc_2$:Pt-$Bu_3$, $Pd(PPh_3)_4$ and $Pd(PPh_3)_2Cl_2$. Example solvents may be dimethylformamide (DMF), N-methylpyrrolidone (NMP), toluene, xylene and dioxane. The reaction is typically heated to a temperature greater than about 100° C., such as, for example, greater than about 150° C. for a period greater than 1 hour, such as, for example, from about 1 hour up to about 24 hours and from about 1 hour to about 12 hours. The semiconductors described herein can be prepared using the procedures described in Y. Terao et al., *Palladium-Catalyzed Cross-Coupling of Benzyl Ketones and α, β-Unsaturated Carbonyl and Phenolic Compounds with o-Dibromoarenes to Produce Cyclic Products*, BULL. CHEM. SOC. JPN. Vol. 72, pp. 2345-2350

(1999) and U.S. patent application Ser. No. 12/689,613, incorporated by reference herein in their entirety.

This reaction for the semiconductor core may be illustrated in the following manner:

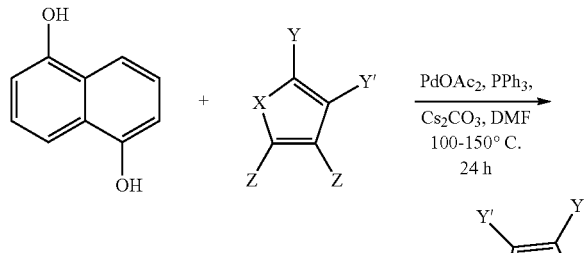

wherein X is a sulfur (S) or a

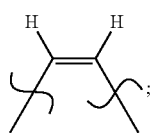

Y and Y' are a hydrogen atom or fused aromatic ring, such as, for example, a fused benzene ring or a fused thiophene ring, and Z is independently a halogen atom, such as, for example, chlorine, bromine, iodine, fluorine.

The small molecule semiconductors described herein can be prepared by first halogenating the benzene-fused or thiophene fused xanthene core. Suitable halogenating reagents include bromine and N-bromosuccinimide. The halogenated xanthene compound is then coupled with a substituted or unsubstituted aryl boronic acid (or ester) or a substituted or unsubstituted heteroaryl boronic acid (or ester). Examples of aryl boronic acids include phenylboronic acid, 4-propylphenylbornic acid. Examples of heteroarylboronic acids include 2-thienylboronic acid and 5-hexyl-2-thienylboronic acid. Such reactions are commonly referred to as "Suzuki couplings".

The semiconductors described herein can also be prepared by other aryl-aryl coupling reactions, such as Yamamoto coupling, Stille coupling, Ullman coupling, or Heck coupling. Examples of suitable cross-coupling reactions are described in U.S. Patent Application Pub. No. 2009/0179198, the disclosure of which is incorporated by reference herein in its entirety. Other cross-coupling reactions are described in Hou et al., *Bandgap and Molecular Energy Level Control of Conjugated Polymer Photovoltaic Materials Based on Benzo[1, 2-b:4,5-b']dithiophene*, MACROMOLECULES, 2008, 41, 6012-6018 and Usta et al. *Air-Stable, Solution-Processable n-Channel and Ambipolar Semiconductors For Thin-Film Transistors Based one the Indenofluorenebis(dicyanovinylene) Core*, J. AM. CHEM. SOC. 2008, 130 (27) 8580-8581.

The reaction for substituting the thiophene fused xanthene core may be illustrated in the following manner:

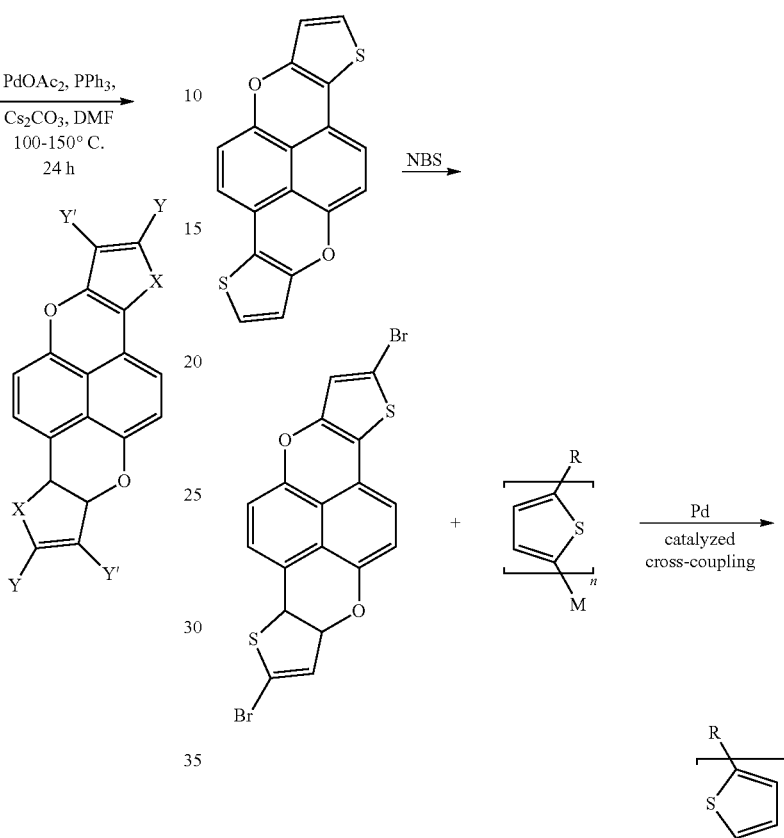

wherein R is independently selected from a hydrogen atom, a substituted or unsubstituted alkyl group, a substituted or unsubstituted alkenyl group, a substituted or unsubstituted ethynyl group, a substituted or unsubstituted aryl group, an alkoxy group, an alkylthio group, an alkylsilyl group, and a halogen atom, wherein n is an integer of from about 1 to about 10, from 1 to about 5 and 1 to about 3, and M is a zinc halide, a magnesium halide, $SnMe_3$, $SnBu_3$, $B(OH)_2$, or a cyclic boronic ester having a formula

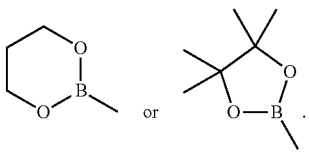

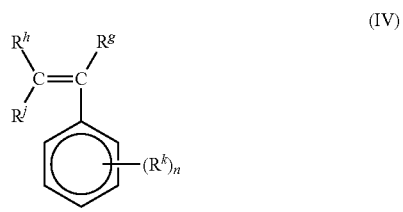

Polymer Binder

The small molecule semiconductor by itself may have poor film-forming properties. Thus, a semiconductor composition may be formed that comprises the small molecule semiconductor of Formula (I) and a polymer binder. This allows a uniform film to be achieved, significantly improving device performance. The polymer binder can be considered as forming a matrix within which the small molecule semiconductor is dispersed.

Any suitable polymer can be used as the polymer binder for the semiconductor composition. In some embodiments, the polymer is an amorphous polymer. The amorphous polymer may have a glass transition temperature less than the melting point temperature of the small molecule semiconductor. In other embodiments, the amorphous polymer has a glass transition temperature greater than the melting point temperature of the small molecule semiconductor. In embodiments, the polymer has a dielectric constant less than 4.5, less than 3.5, including less than 3.0, as measured at 60 Hz at room temperature. In embodiments, the polymer is selected from polymers containing only C, H, F, Cl, or N atoms. In some embodiments, the polymer is a low polarity polymer, such as a hydrocarbon polymer or a fluorocarbon polymer without any polar groups. For example, polystyrene is an amorphous polymer and has a dielectric constant about 2.6. A list of other low polarity polymers includes but is not limited to the following: fluoropolyarylether, poly(p-xylylene), poly(vinyl toluene), poly(α-methyl styrene), poly(vinyl naphthalene), polyethylene, polypropylene, polyisoprene, poly(tetrafluoroethylene), poly(chlorotrifluoroethylene), poly(2-methyl-1,3-butadiene), poly(cyclohexyl methacrylate), poly(chlorostyrene), poly(4-methyl styrene), poly(vinylcyclohexane), polyphenylene, poly-p-phenylvinylidenes, poly(arylene ether), polyisobutylene, poly(2,6-dimethyl-1,4-phenylene ether), poly[1,1-(2-methyl propane) bis-(4-phenyl)carbonate], poly(α-α-α'-α'tetrafluoro-p-xylylene), fluorinated polyimide, poly(ethylene/tetrafluoroethylene), poly(ethylene/chlorotrifluoroethylene), fluorinated ethylene/propylene copolymer, poly(styrene-co-α-methyl styrene), poly(styrene/butadiene), poly(styrene/2,4-dimethylstyrene), CYTOP, poly(propylene-co-1-butene), poly(styrene-co-vinyl toluene), poly(styrene-block-butadiene-block-styrene), poly(styrene-block-isopene-block-styrene), terpene resin, poly(N-vinylcarbazole), polycarbazole, polytriarylamine, and the like.

Exemplary polymer binders suitable for the semiconductor composition include polystyrene, poly(α-methyl styrene), poly(4-methyl styrene), poly(α-methyl styrene-co-vinyl toluene), poly(styrene-block-butadiene-block-styrene), poly(styrene-block-isoprene-block-styrene), poly(vinyl toluene), a terpene resin, poly(styrene-co-2,4-dimethylstyrene), poly(chlorostyrene), poly(styrene-co-α-methyl styrene), poly(styrene-co-butadiene), polycarbazole, a polytriarylamine, or poly(N-vinylcarbazole).

A styrene-based polymer, in particular, is believed to be a suitable polymer binder. Styrene-based polymers contain a repeating unit derived from a styrene monomer of Formula (IV):

$$(IV)$$

wherein $R^g$, $R^h$, $R^j$, and $R^k$ are independently hydrogen, halogen, and $C_1$-$C_{20}$ alkyl; and n is an integer from 0 to 5. The styrene monomer can be styrene ($R^g$, $R^h$, and $R^j$ are all hydrogen, n=0), alpha-methyl styrene ($R^g$ is methyl, $R^h$ and $R^j$ are hydrogen, n=0), or 4-methyl styrene ($R^g$, $R^h$, and $R^j$ are all hydrogen, n=1, $R^k$ is methyl in the 4-position).

In particular embodiments, the styrene-based polymer may have a weight average molecular weight of from about 40,000 to about 2,000,000, from about 50,000 to about 1,000,000, from about 50,000 to about 500,000 and from about 75,000 to about 250,000. Furthermore, if included with small molecule semiconductor, the weight ratio of the small molecule semiconductor to the polymer binder may be from 5:1 to 2:3, from 3:1 to 5:6 and 2:1 to 1:1.

The polymer binder may be present in the semiconductor composition in an amount of from about 0.1 to about 10%, from about 0.1 to about 2%, from about 0.5 to about 2% and from about 0.5 to about 1%.

Solvents

The semiconductor composition is soluble or substantially soluble in common coating solvents and thus may form a semiconductor solution comprised of the material in an organic solvent. For example, in embodiments, the small molecule semiconductor and/or the polymer binder possess a solubility of at least about 0.1 percent by weight, and more specifically, from about 0.3 percent to about 10 percent, or to about 50 percent by weight in such solvents as chlorinated solvents such as chlorobenzene, chlorotoluene, dichlorobenzene, dichloroethane, and the like; alcohols and diols such as propanol, butanol, hexanol, hexanediol, and the like; hydrocarbons or aromatic hydrocarbons such as hexane, heptane, toluene, xylene, ethyl benzene, and the like; ketones such as acetone, methyl ethyl ketone, and the like.; acetates, such as ethyl acetate; pyridine, tetrahydrofuran, and the like. Moreover, the small molecule semiconductors of the formulas as illustrated herein provide a stable conductivity of, for example, from about $10^{-9}$ S/cm to about $10^{-4}$ S/cm, and more specifically, from about $10^{-8}$ S/cm to about $10^{-5}$ S/cm as determined by conventional four-probe conductivity measurements.

The solvent may be present in the semiconductor solution in an amount of from about 50 to about 99.9 wt. %, from about 80 to about 99.5 wt. %, from about 90 to about 99 wt. % and from about 95 to about 99 wt. %, based upon the weight of the semiconductor solution.

Fabrication of a printed organic electronic (POE) device using the semiconductor solution can be carried out by depositing the semiconductor solution on a substrate using any suitable liquid deposition technique at any suitable time prior to or subsequent to the formation of other optional layer or layers on the substrate. Thus, liquid deposition of the semiconductor solution on the substrate can occur either on a substrate or on a substrate already containing layered material, for example, a semiconductor layer and/or an insulating layer of a thin-film transistor.

The phrase "liquid deposition technique" refers to, for example, deposition of a composition using a liquid process such as liquid coating or printing technique, where the liquid is a homogeneous or heterogeneous dispersion of the small molecule semiconductors in a solvent. Furthermore, the semiconductor solution may be deposited in any suitable pattern on the substrate.

Examples of liquid coating processes may include, for example, spin coating, blade coating, rod coating, dip coating, and the like. Examples of printing techniques may include, for example, lithography or offset printing, gravure, flexography, screen printing, stencil printing, inkjet printing, stamping (such as microcontact printing), and the like. In embodiments, liquid deposition of the semiconductor solution deposits a layer of the small molecule semiconductor having a thickness ranging from about 5 nanometers to about 5 millimeters, from about 10 nanometers to about 1000 micrometers, from about 100 nanometers to about 500 micrometers, from about 1 micrometer to about 100 micrometers and from about 5 micrometers to about 25 micrometers. The deposited semiconductor solution at this stage may or may not exhibit appreciable electrical conductivity.

Heating the semiconductor solution at a temperature of, for example, at or below about 150° C. or at or below about 130° C., such as, for example, from about 50° C. to about 150° C., from about 50° C. to about 130° C., from about 50° C. to about 80° C., from about 100° C. to about 130° C. and from about 100° C. to about 120° C., to remove the solvent from the semiconductor solution and thus form a layer comprising the small molecule semiconductors of Formula (1) on the substrate. The heating temperature is one that does not cause adverse changes in the properties of previously deposited layer(s) or the substrate (whether single layer substrate or multilayer substrate) and the heating temperature is related to the temperature following deposition.

The heating can be performed for a time ranging from, for example, 1 second to about 10 hours and from about 10 seconds to 1 hour. The heating can be performed in air, in an inert atmosphere, for example, under nitrogen or argon, or in a reducing atmosphere, for example, under nitrogen containing from 1 to about 20 percent by volume hydrogen. The heating can also be performed under normal atmospheric pressure or at a reduced pressure of, for example, from about 1000 mbars to about 0.01 mbars.

As used herein, the term "heating" encompasses any technique(s) that can impart sufficient energy to remove the solvent from the substrate. Examples of heating techniques may include thermal heating (for example, a hot plate, an oven, and a burner), infra-red ("IR") radiation, a laser beam, microwave radiation, or UV radiation, or a combination thereof.

Electronic Devices

The small molecule semiconductor of Formula (1), upon being deposited in a semiconductor layer, may be used in electronic devices such as thin-film transistors (TFT), diodes and photovoltaic devices, such as polymer solar cells (PSCs). The use of the semiconductor in electronic devices is illustrated herein using thin-film transistors.

In embodiments, there is provided a thin-film transistor comprising:
(a) a gate dielectric layer;
(b) a gate electrode;
(c) a semiconductor layer;
(d) a source electrode;
(e) a drain electrode; and
(f) a substrate layer wherein the gate dielectric layer, the gate electrode, the semiconductor layer, the source electrode, the drain electrode and the substrate layer are in any sequence as long as the gate electrode and the semiconductor layer both contact the gate dielectric layer, and the source electrode and the drain electrode both contact the semiconductor layer, and the semiconductor layer is comprised of the small molecule semiconductor compounds described herein.

The substrate layer may generally be a silicon material inclusive of various appropriate forms of silicon, a glass plate, a plastic film or a sheet, and the like depending on the intended applications. For structurally flexible devices, a plastic substrate, such as for example polyester, polycarbonate, polyimide sheets, and the like, may be selected. The thickness of the substrate may be, for example, from about 10 micrometers to about 100 millimeters with a specific thickness being from about 50 to about 100 micrometers, especially for a flexible plastic substrate, and from about 1 to about 10 millimeters for a rigid substrate such as glass or silicon.

The gate dielectric layer, which can separate the gate electrode from the source and drain electrodes, and in contact with the semiconductor layer, can generally be an inorganic material film, an organic polymer film, or an organic-inorganic composite film. The thickness of the gate dielectric layer can be, for example, from about 10 nanometers to about 1 micrometer with a more specific thickness being about 100 nanometers to about 500 nanometers. Examples of inorganic materials suitable as the dielectric layer may include silicon oxide, silicon nitride, aluminum oxide, barium titanate, barium zirconate titanate and the like. Examples of organic polymers for the dielectric layer may include polyesters, polycarbonates, poly(vinyl phenol), polyimides, polystyrene, poly(methacrylate)s, poly(acrylate)s, epoxy resin and the like. Examples of inorganic-organic composite materials may include nanosized metal oxide particles dispersed in polymers, such as polyester, polyimide, epoxy resin and the like. The gate dielectric layer is generally of a thickness of from about 50 nanometers to about 500 nanometers depending on the dielectric constant of the dielectric material used. More specifically, the dielectric material has a dielectric constant of, for example, at least about 3, thus a suitable dielectric thickness of about 300 nanometers can provide a desirable capacitance, for example, of about $10^{-9}$ to about $10^{-7}$ F/cm$^2$.

In the present disclosure, the dielectric layer may be surface modified with a surface modifier. Exemplary surface modifiers include organosilanes, such as hexamethyldisilazane (HMDS), phenyltrichlorosilane, octyltrichlorosilane (OTS-8), and octadecyltrichlorosilane (ODTS-18). The semiconducting layer can be directly contacted with this modified dielectric layer surface. The contact may be complete or partial. This surface modification can also be considered as forming an interfacial layer between the dielectric layer and the semiconducting layer.

Situated, for example, between and in contact with the dielectric layer and the source/drain electrodes is the active semiconductor layer comprised of small molecule semiconductors of the Formulas as illustrated herein, and wherein the thickness of this layer is generally, for example, about 5 nanometers to about 1 micrometer, about 5 nanometers to about 500 nanometers or about 40 nanometers to about 100 nanometers. This layer can generally be fabricated by solution processes such as spin coating, casting, screen, stamp, or jet printing of a solution of small molecule semiconductors of the present disclosure. In certain configurations, the semiconducting layer completely covers the source and drain electrodes.

The gate electrode can be a thin metal film, a conducting polymer film, a conducting film generated from a conducting ink or paste, or the substrate itself (for example heavily doped silicon). Examples of the gate electrode materials may include gold, silver, chromium, indium tin oxide, conducting polymers, such as polystyrene sulfonate-doped poly(3,4-ethylenedioxythiophene) (PSS/PEDOT), a conducting ink/paste comprised of carbon black/graphite or colloidal silver dispersion contained in a polymer binder, such as Electrodag available from Acheson Colloids Company, and silver filled electrically conductive thermoplastic ink available from Noelle Industries, and the like. The gate layer may be prepared by vacuum evaporation, sputtering of metals or conductive metal oxides, coating from conducting polymer solutions or conducting inks, or dispersions by spin coating, casting or printing. The thickness of the gate electrode layer may be, for example, from about 10 nanometers to about 10 micrometers, and a specific thickness may be, for example, from about 10 to about 200 nanometers for metal films, and about 1 to about 10 micrometers for polymer conductors.

The source and drain electrode layer can be fabricated from materials which provide a low resistance ohmic contact to the semiconductor layer. Typical materials suitable for use as source and drain electrodes may include those of the gate electrode materials such as gold, nickel, aluminum, platinum, conducting polymers, and conducting inks. Typical thickness of this layer may be, for example, from about 40 nanometers to about 1 micrometer with the more specific thickness being about 100 to about 400 nanometers. The TFT devices contain a semiconductor channel with a width W and length L. The semiconductor channel width may be, for example, from about 10 micrometers to about 5 millimeters with a specific channel width being about 100 micrometers to about 1 millimeter. The semiconductor channel length may be, for example, from about 1 micrometer to about 1 millimeter with a more specific channel length being from about 5 micrometers to about 100 micrometers.

The source electrode is grounded and a bias voltage of generally, for example, about 0 volts to about −80 volts is applied to the drain electrode to collect the charge carriers transported across the semiconductor channel when a voltage of generally, for example, about +10 volts to about −80 volts is applied to the gate electrode.

In embodiments, the annealing temperature for a thin-film transistor comprised of a small molecule semiconductor layer having the small molecule semiconductor compounds according to the Formulas herein is about or below about 150° C., about or below about 125° C. or about or below about 100° C.

The performance of a thin-film transistor can be measured by mobility. The mobility is measured in units of $cm^2/V \cdot sec$, and higher mobility is desired. The resulting thin-film transistor using the semiconductor composition of the present disclosure may have a field effect mobility of at least 0.01 $cm^2/V \cdot sec$. The TFT of the present disclosure may have a current on/off ratio of at least $10^3$.

FIG. 1 illustrates a TFT configuration comprised of a substrate (16) in contact with a gate electrode (18) and with a gate dielectric layer (14) containing the gate electrode (18). On top of the gate dielectric layer (14) are the source electrode (20) and the drain electrode (22). Above and situated between the source electrode (20) and the drain electrode (22) is the small molecule semiconductor layer (12). The gate electrode (18) can be included in the substrate (16), in the gate dielectric layer (14), and the like throughout.

The various components of the TFT may be deposited upon the substrate in any order. Generally, however, the gate electrode and the semiconducting layer should both be in contact with the gate dielectric layer. In addition, the source and drain electrodes should both be in contact with the semiconducting layer. The phrase "in any order" includes sequential and simultaneous formation. For example, the source electrode and the drain electrode can be formed simultaneously or sequentially. The term "on" or "upon" the substrate refers to the various layers and components with reference to the substrate as being the bottom or support for the layers and components that are on top of it. In other words, all of the components are on the substrate, even though they do not all directly contact the substrate. For example, both the dielectric layer and the semiconductor layer are on the substrate, even though one layer is closer to the substrate than the other layer. The resulting TFT has good mobility and good current on/off ratio.

Figure 2:
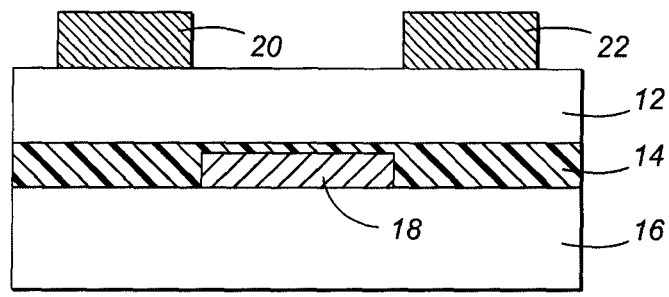

FIG. 2 illustrates a TFT configuration comprised of a substrate (16) in contact with a gate electrode (18) and with a gate dielectric layer (14) containing the gate electrode (18). On top of the gate dielectric layer (14) is the small molecule semiconductor layer (12). Above the small molecule semiconductor layer (12) are the source electrode (20) and the drain electrode (22).

Other known suitable materials not recited herein for the various components of the TFT devices of the present disclosure can also be selected in embodiments.

In embodiments, the small molecule semiconductors described herein may also be used in photovoltaic devices, such as polymer solar cells (PSCs). The inclusion of the small molecule semiconductors described may lead to a photovoltaic device with a lower manufacturing cost, possess a low band gap polymer for broad light absorption that leads to increased efficiency in the photovoltaic device and is lightweight and has increased flexibility when compared to silicon solar cells.

In embodiments, there is provided a photovoltaic device comprising:
(a) a first electrode;
(b) a second electrode;
(c) a thin-film layer; and
(d) a substrate
wherein the substrate, the first electrode, the second electrode and the thin-film layer are in any sequence as long as the first electrode and the second electrode both contact the thin-film layer, and the thin-film layer is comprised of the small molecule semiconductor compounds described herein.

In embodiments and with further reference to the present disclosure, the substrate layer may generally be a silicon material inclusive of various appropriate forms of silicon, a glass plate, a plastic film or a sheet, and the like depending on the intended applications. For structurally flexible devices, a plastic substrate, such as for example polyester, polycarbonate, polyimide sheets, and the like, may be selected. The thickness of the substrate may be, for example, from about 10 micrometers to about 100 millimeters with a specific thickness being from about 50 to about 100 micrometers, especially for a flexible plastic substrate, and from about 1 to about 10 millimeters for a rigid substrate such as glass or silicon.

Situated, for example, between and in contact with the first and second electrode is the thin-film layer comprised of small molecule semiconductors of the formulas as illustrated herein, and wherein the thickness of this layer is generally, for example, about 10 nanometers to about 1 micrometer, or about 40 to about 100 nanometers. This layer can generally be fabricated by solution processes such as spin coating, casting, screen, stamp, or jet printing of a solution of small molecule semiconductors of the present disclosure.

The first and second electrode can be a thin metal film, a conducting polymer film, a conducting film generated from a conducting ink or paste, or the substrate itself (for example heavily doped silicon). Examples of the first and second electrode materials may include silver, gold, chromium, fluorine-doped tin oxide ("FTO"), $ZnO$—$Ga_2O_3$, $ZnO$—$Al_2O_3$, and $SnO_2$—$Sb_2O_3$, indium tin oxide, conducting polymers, such as polystyrene sulfonate-doped poly(3,4-ethylenedioxythiophene) (PSS/PEDOT), a conducting ink/paste comprised of carbon black/graphite or colloidal silver dispersion contained in a polymer binder, such as Electrodag available from Acheson Colloids Company, and silver filled electrically conductive thermoplastic ink available from Noelle Industries, and the like. The first electrode and/or second electrode layer be prepared by vacuum evaporation, sputtering of metals or conductive metal oxides, coating from conducting semiconductor solutions or conducting inks, or dispersions by spin coating, casting or printing. The thickness of the first and/or second electrode layer may be, for example, from about 10 nanometers to about 10 micrometers, and a specific thickness may be, for example, from about 10 to about 200 nanometers for metal films, and about 1 to about 10 micrometers for polymer conductors.

EXAMPLES

Example 1

Synthesis of a Benzene Fused Xanthene

In a 50 mL Schlenk flask, cesium carbonate ($Cs_2CO_3$) (9.77 g, 30.0 mmol), palladium (II) acetate (0.07 g, 0.312 mmol), triphenylphosphine (0.328 g, 1.250 mmol) and naphthalene-1,5-diol (0.801 g, 5 mmol) were added under an argon (Ar) atmosphere. The flask was then evacuated under high vacuum and purged with Ar. The mixture was then treated with anhydrous dimethylformamide (DMF) (volume: 20 ml) and 1,2-dibromobenzene (1.447 ml, 12.00 mmol). After stirring at room temperature for 5 minutes, the treated mixture was heated to 140° C. under an Ar atmosphere. After 24 hours, the heating source was removed and the heated reaction was cooled to room temperature. The DMF was removed by vacuum distillation and the solid residue was re-suspended in $CH_2Cl_2$ (200 mL) and filtered through celite to remove the solids from the reaction mixture. The filtrate was concentrated using a rotary evaporator and purified by column chromatography yielding 150 mg of a benzene-fused xanthene as a yellow solid. The structure was confirmed by $^1H$ NMR spectroscopy.

Example 2

Synthesis of a Thiophene Fused Xanthene

In a Schlenk flask, cesium carbonate (9.76 g, 30.0 mmol), naphthalene-1,5-diol (0.8 g, 4.99 mmol), palladium (II) acetate (0.063 g, 0.281 mmol) and triphenylphosphine (0.301 g, 1.149 mmol) is added under an Ar atmosphere. The flask can then be evacuated under high vacuum and purged with Ar (2x). Anydrous DMF (20 mL) is then added and the flask is then evacuated under vacuum and purged with Ar. The reaction is then treated with 2,3-dibromothiophene (1.330 ml, 11.99 mmol) and heated to 140° C. under an Ar atmosphere. After stirring the heated mixture at 140° C. for 24-48 hours, the heating source is removed and the reaction is cooled to room temperature. DMF is removed by vacuum distillation and the solid residue is re-suspended in $CH_2Cl_2$ (200 mL) and is filtered through celite to remove the solids from the reaction mixture. The filtrate was concentrated using a rotary evaporator the residue is purified using standard methods known is the art. The thiophene fused xanthene compound is then isolated as a pure solid.

The thiophene fused xanthene compound is then brominated with N-bromosuccumide and coupled with 5-hexylthienylboronic acid using standard Suzuki cross-coupling methods, as shown below in the reaction scheme.

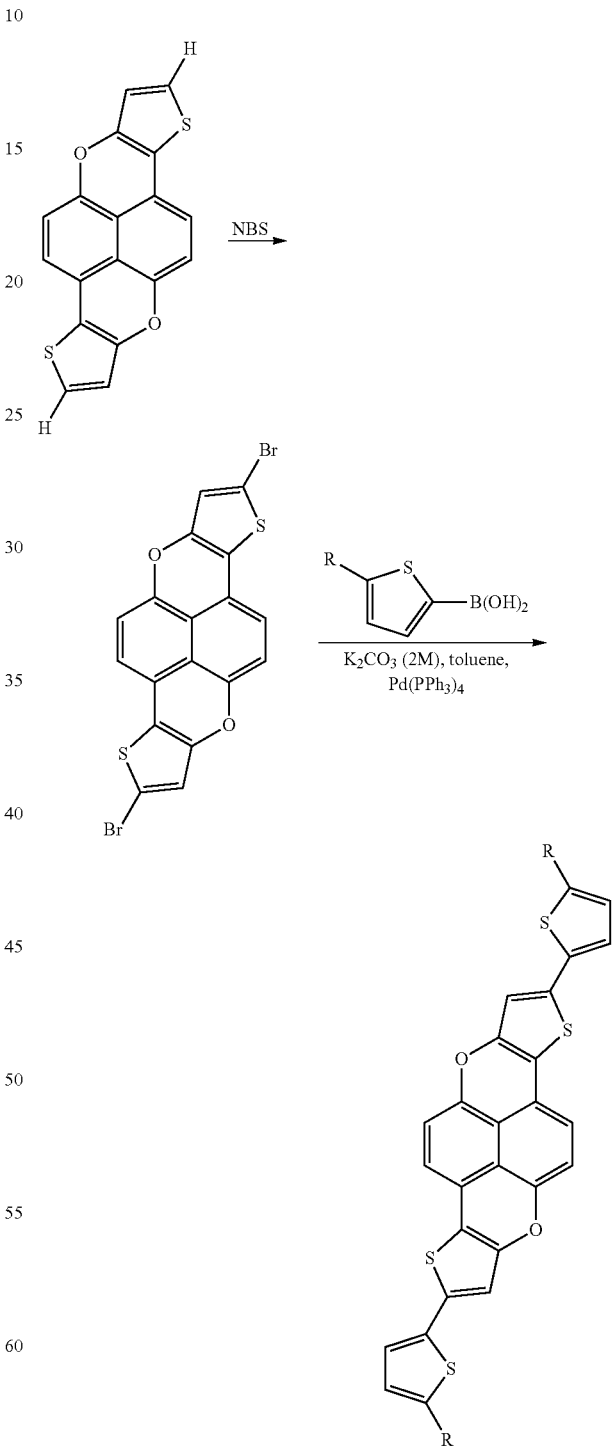

R = n-hexyl

Figure 3:
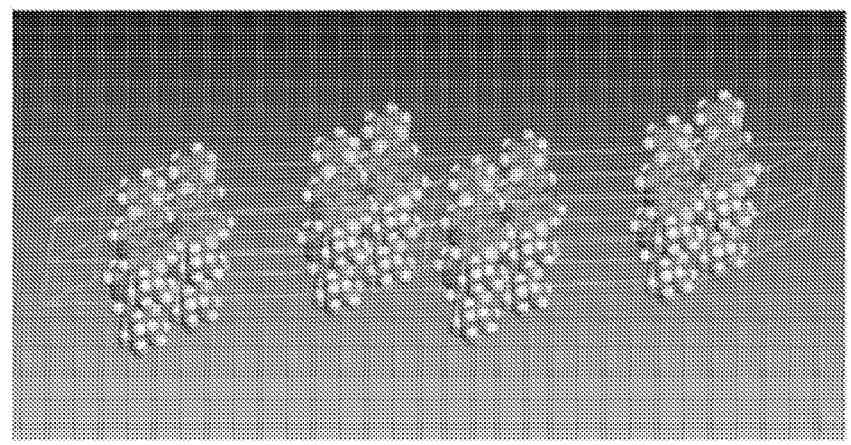
FIG. 3 shows a color model of the equilibrium geometry and simulated crystal structure of 2,8-bis(5-hexylthiophen-2-yl)thieno[3',2':2,3]chromeno[6,5,4-def]thieno[3,2-b]chromene.

FIG. 3 is a model illustrating the equilibrium geometry and crystal structure of 2,8-bis(5-hexylthiophen-2-yl)thieno[3',2':2,3]chromeno[6,5,4-def]thieno[3,2-b]chromene, a compound of Formula (II) wherein $R_1$ and $R_2$ are $C_6H_{13}$ and m is 1. The model was formed in Materials Studio 5.5 using the DMol3 package to determine equilibrium geometry and the Polymorph module with the Compass Force Field to predict the crystal structure. The crystal polymorph shown in FIG. 3 shows the molecules aligned in stacks due to π-π stacking, which facilitates hole transport. The alkyl chains (hexyl chains) are aligned parallel to the aromatic stacks and should provide longer range order in the solid state.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What is claimed is:

1. A small molecule semiconductor of Formula (I-c) or (I-d):

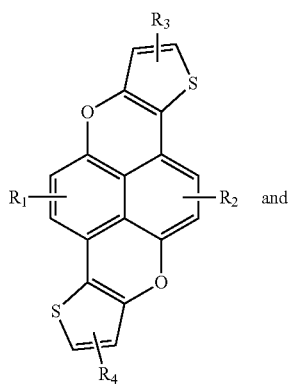

(I-c)

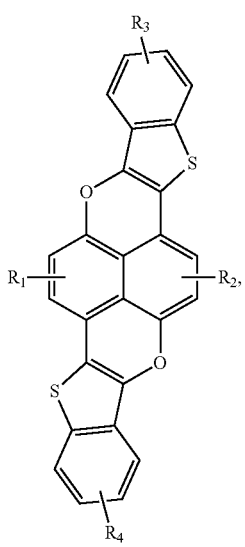

(I-d)

wherein $R_1$, $R_2$, $R_3$ and $R_4$ are independently selected from a hydrogen atom, a substituted or unsubstituted alkyl group, a substituted or unsubstituted alkenyl group, a substituted or unsubstituted ethynyl group, a substituted or unsubstituted aryl group, a substituted or unsubstituted heteroaryl group, an alkoxy group, an alkylthio group, an alkylsilyl group, a cyano group, and a halogen atom.

2. The small molecule semiconductor of claim 1, wherein $R_1$ and $R_2$ are hydrogen atoms.

3. The small molecule semiconductor of claim 1, wherein $R_1$ and $R_2$ in Formulas (I-c) and (I-d) are independently selected from the group consisting of a hydrogen atom, an alkyl group, a cyano group and a halogen atom.

4. The small molecule semiconductor of claim 3, wherein the small molecule semiconductor has the structure of Formula (II)

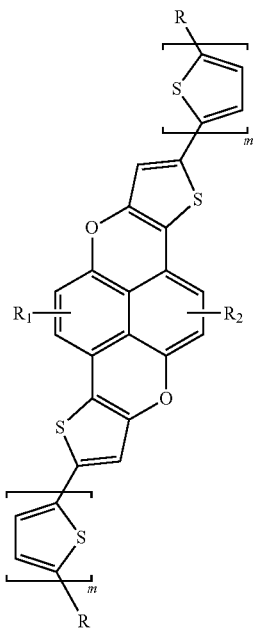

(II)

wherein $R_1$ and $R_2$ in Formula (II) are hydrogen atoms, wherein R is independently selected from a substituted or unsubstituted alkyl group, a substituted or unsubstituted alkenyl group, a substituted or unsubstituted ethynyl group, a substituted or unsubstituted aryl group, an alkoxy group, an alkylthio group, an alkylsilyl group, and a halogen atom, and wherein m is from 1 to 5.

5. A semiconductor composition comprising:
a polymer binder; and a small molecule semiconductor of Formula (I-c) or (I-d):

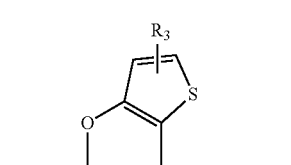
(I-c)

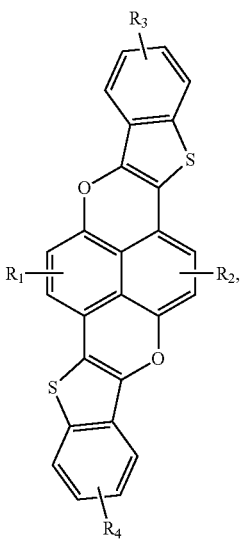
(I-d)

wherein $R_1$, $R_2$, $R_3$ and $R_4$ are independently selected from a hydrogen atom, a substituted or unsubstituted alkyl group, a substituted or unsubstituted alkenyl group, a substituted or unsubstituted ethynyl group, a substituted or unsubstituted aryl group, a substituted or unsubstituted heteroaryl group, an alkoxy group, an alkylthio group, an alkylsilyl group, a cyano group, and a halogen atom.

6. The semiconductor composition of claim 5, wherein $R_1$ and $R_2$ are hydrogen atoms.

7. The semiconductor composition of claim 5, wherein $R_1$ and $R_2$ in Formulas (I-c) and (I-d) are independently selected from the group consisting of a hydrogen atom, an alkyl group, a cyano group and a halogen atom.

8. The semiconductor composition of claim 5, wherein the polymer binder is polystyrene, poly(a-methyl styrene), poly(4-methyl styrene), poly(alpha-methyl styrene-co-vinyl toluene), poly(styrene-block-butadiene-block-styrene), poly(styrene-block-isopene-block-styrene), poly(vinyl toluene), a terpene resin, poly(styrene-co-2,4-dimethylstyrene), poly(chlorostyrene), poly(styrene-co-a-methyl styrene), poly(styrene-co-butadiene), a polycarbazole, a polytriarylamine, poly(N-vinylcarbazole), or mixtures thereof.

9. The semiconductor composition of claim 5, wherein the polymer binder is a styrene-based polymer.

10. An electronic device comprising a semiconducting layer, the semiconducting layer comprising:

a small molecule semiconductor of Formula (I-c) or (I-d):

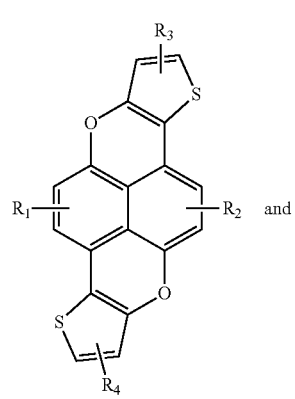
(I-c)

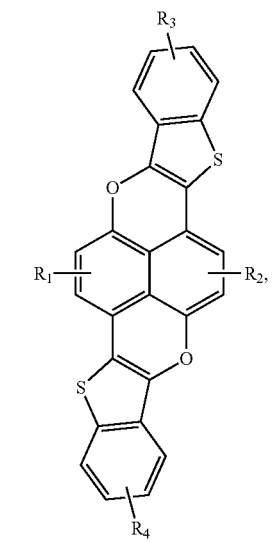
(I-d)

wherein $R_1$, $R_2$, $R_3$ and $R_4$ are independently selected from a hydrogen atom, a substituted or unsubstituted alkyl group, a substituted or unsubstituted alkenyl group, a substituted or unsubstituted ethynyl group, a substituted or unsubstituted aryl group, a substituted or unsubstituted heteroaryl group, an alkoxy group, an alkylthio group, an alkylsilyl group, a cyano group, and a halogen atom.

11. The electronic device of claim 10, wherein $R_1$ and $R_2$ are hydrogen atoms.

12. The electronic device of claim 10, wherein $R_1$ and $R_2$ in Formulas (I-c) and (I-d) are independently selected from the group consisting of a hydrogen atom, an alkyl group, a cyano group and a halogen atom.

13. The electronic device of claim 10, wherein the semiconducting layer further comprises a polymer binder.

14. The electronic device of claim 10, wherein the polymer binder is polystyrene, poly(a-methyl styrene), poly(4-methyl styrene), poly(alpha-methyl styrene-co-vinyl toluene), poly(styrene-block-butadiene-block-styrene), poly(styrene-block-isopene-block-styrene), poly(vinyl toluene), a terpene resin, poly(styrene-co-2,4-dimethylstyrene), poly(chlorostyrene), poly(styrene-co-a-methyl styrene), poly(styrene-co-butadiene), a polycarbazole, a polytriarylamine, poly(N-vinylcarbazole), or mixtures thereof.

15. The electronic device of claim 10, wherein the polymer binder is a styrene-based polymer.

16. The electronic device of claim 10, the electronic device further comprising a dielectric layer;
   wherein the dielectric layer comprises a modified surface; and
   wherein the semiconducting layer is in direct contact with the modified surface.

17. The electronic device of claim 16, wherein the modified surface has been modified with an organosilane.

* * * * *